United States Patent [19]

Miller

[11] 4,385,318
[45] May 24, 1983

[54] METHOD AND APPARATUS FOR COMPARING DATA SIGNALS IN A CONTAINER INSPECTION DEVICE

[75] Inventor: John W. V. Miller, Toledo, Ohio
[73] Assignee: Owens-Illinois, Inc., Toledo, Ohio
[21] Appl. No.: 205,053
[22] Filed: Nov. 7, 1980
[51] Int. Cl.³ .......................... H04N 5/19; H04N 7/18
[52] U.S. Cl. .................................... 358/106; 328/160; 328/161; 358/160; 358/282
[58] Field of Search ............... 358/106, 280, 282, 160; 356/430, 431, 237, 239; 250/563, 572; 328/158, 160, 161; 364/606

[56] References Cited

U.S. PATENT DOCUMENTS 3,379,826  4/1968  Gray .................................... 358/282
4,054,377  10/1977  Gibson ................................ 356/430
4,246,606  1/1981  Yoshida .............................. 358/106

Primary Examiner—Joseph A. Orsino, Jr.
Attorney, Agent, or Firm—Gerald T. Welch; Myron E. Click; David H. Wilson

[57] ABSTRACT

The present invention relates to an apparatus and method for generating a comparison signal representing the magnitude difference between two successive video signals representing adjacent inspection points on the container. One of the two video signals is multiplied by a first predetermined value to generate a first product signal. The first product signal and the other one of the two video signals are combined to generate a second product signal having a magnitude representing the ratio between the other one of the two video signals and the first product signal with the first product signal as the denominator. A signal having a second predetermined value is then subtracted from the second product signal to generate the comparison signal. A comparison signal generated in this manner is insensitive to general light variations across the container.

15 Claims, 3 Drawing Figures

METHOD AND APPARATUS FOR COMPARING DATA SIGNALS IN A CONTAINER INSPECTION DEVICE

CROSS-REFERENCE TO RELATED APPLICATION

The present invention is related to the sidewall inspection device disclosed in U.S. patent application Ser. No. 205,054, filed Nov. 7, 1980, in the name of John W. V. Miller and entitled "Method and Apparatus for Rapidly Extracting Significant Data from a Sparse Object", assigned to the assignee of the present application, and incorporated herein by reference.

BACKGROUND OF THE INVENTION

1. Field of the Invention

The present invention relates in general to sidewall inspection devices for containers and in particular to a method and apparatus for comparing individual video data signals generated from an inspection of a container, such as a glass bottle.

2. Description of the Prior Art

The use of optical scanning devices for inspecting the sidewalls of containers is well known. Numerous devices, such as those shown in U.S. Pat. Nos. 3,708,680 and 3,716,136, have circuitry including means for receiving and interpreting light passed through or directed onto an item under inspection. Such devices incorporate either a visual display for comparison of the item or employ a device capable of producing a resistance proportional to the intensity of light directed thereon. Whether the output of such a device is visual or electrical in nature, it is eventually compared against a model to determine if the item under inspection is suitable as to size and construction and is without flaws, cracks, or foreign objects. Such devices are each intended to provide an automated inspection means for checking single or multiple objects, as in a moving column of bottles. U.S. Pat. No. 3,877,821 discloses an apparatus having a scanning array that is serially interrogated to generate a train of pulses having amplitudes representing the light transmitted through an object under inspection. Adjacent pulses are compared to generate pulses having amplitudes which represent the difference in the adjacent pulse amplitudes. The difference pulses can be utilized to indicate a defect in the object being inspected. U.S. Pat. No. 3,942,001 discloses an apparatus for detecting the presence of extraneous matter or cracks in translucent containers. A beam of light is projected through the container to generate an inspection signal which is compared with an acceptance signal. The acceptance signal amplitude is varied in accordance with the position of the spot beam with respect to the container.

One of the problems associated with prior art inspection devices is the sensitivity of the inspection device to general light variations across the container. For example, in the above discussed U.S. Pat. No. 3,877,821, the amplitude of the difference pulse varies in accordance with the intensity of the light. Thus, if the intensity of light varies across the container, a difference pulse representing one type of defect in one portion of the container may be different in amplitude than a difference pulse representing a similar defect in another portion of the container subject to a different intensity of light.

SUMMARY OF THE INVENTION

The present invention is concerned with a method and apparatus for comparing video data signals generated from an inspection of a container in which the comparison is insensitive to general light variations across the container. A light source and camera are utilized to generate a series of video signals each having a magnitude corresponding to the amount of light received from a particular point of inspection, or pixel, on the container. Successive video signals represent adjacent pixels on the container.

A comparison circuit is responsive to the video signals for generating a comparison signal representing the magnitude difference between two successive video signals. The comparison circuit includes means such as an amplifier for multiplying one of the two successive video signals by a first predetermined value to generate a first product signal. The comparison circuit also includes means such as a sample/hold circuit for storing the first one of the two successive video signals. If the first video signal is also the signal which is multiplied by a first predetermined value, the amplifier can be connected ahead of the sample/hold circuit such that the first product signal, and not the first video signal, is stored.

The first product signal and the other one of the two successive video signals are then combined to generate a second product signal having a magnitude representing the ratio between the other one of the two successive video signals and the first product signal. The ratio is calculated with the first product signal as the denominator. Next, the second product signal is added to a second predetermined value to generate the comparison signal. Typically, the gain of the amplifier, i.e., the first predetermined value, is the reciprocal of the second predetermined value. The comparison signal can then be compared with a corresponding threshold signal to determine whether a defect has been detected. If the comparison signal exceeds the threshold signal, an event signal can be generated to signal the detection of a defect.

DESCRIPTION OF THE PREFERRED EMBODIMENT

Figure 1:
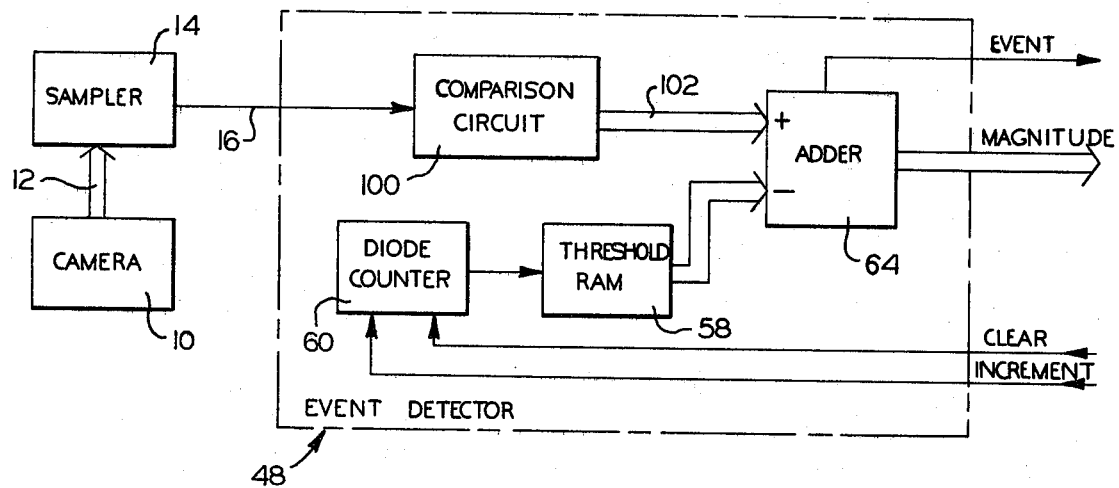
FIG. 1 is a block diagram of a portion of an inspection device to which the present invention is applicable.

Referring to FIG. 1, there is shown in block diagram form a portion of a sidewall inspection device for detecting defects in objects such as containers. Although FIG. 1 will be discussed briefly, a more detailed description of those elements shown in FIG. 1 and the remaining portion of the inspection device not shown in FIG. 1 can be found in the above-identified U.S. application entitled "Method and Apparatus for Rapidly Extracting Significant Data from a Sparse Object", which is herein incorporated by reference. It should be noted that the reference numerals herein which are less than 100 correspond directly to elements which have been discussed in detail in the above-identified U.S. patent application.

In FIG. 1, an object, such as a glass bottle (not shown), is scanned by a camera 10. The camera 10 generates a plurality of signals proportional in magnitude to the amount of light received from the glass bottle. In the preferred embodiment of the invention, a light source (not shown) directs a beam of light through the glass bottle under inspection and into the camera 10. The camera 10 includes a plurality of photosensitive devices, such as photodiodes, which are vertically arranged in a linear array. It has been found that a linear array of two hundred fifty-six photodiodes yields satisfactory results. A photodiode is a variable resistance device that will pass a voltage proportional to the amount of light falling thereon. Each photodiode receives light which has passed through a different inspection point of the bottle. An inspection point is typically referred to as a pixel. If a flaw, crack, or foreign object is contained in the bottle, then the light passing through the corresponding pixel of the bottle will be partially blocked or reflected and the corresponding photodiode will register a different intensity of light than if no defect had been present.

The signals from the photodiodes of the camera 10 are supplied to a sampler 14 on a plurality of lines 12. Each of the photodiodes is sampled in a sequential order to produce a series of video pulse signals on a line 16 which represent the amount of light which has passed through the bottle under inspection along one vertical sequential check of the photodiodes. The sampler 14 is a device well known in the art and forms no part of the invention. By rotating the bottle under inspection relative to the camera 10, a plurality of different sweeps can be made, each sweep inspecting a different portion of the bottle. It has been found that about three hundred seventy-five to four hundred different sweeps will sufficiently cover an average bottle and ensure an accurate inspection. Thus, the sampler 14 generates a plurality of video signals series on the line 16, each signal having a magnitude proportional to the amount of light passing through the respective pixel of the bottle.

The video signals generated by the sampler 14 on the line 16 are an input to an event detector 48 which represents a portion of the inspection device referred to as an inspection device interface 18 (not shown in the drawings). The interface 18, which is discussed in detail in the above-identified incorporated reference, functions to rapidly extract significant data from the glass bottle in a manner which is suitable for computer analysis.

The event detector 48 includes a comparison circuit 100 which receives the video signals on the line 16 and generates a digital comparison signal on a line 102 to an adder 64. In the above-identified incorporated reference, the comparison circuit 100 comprises a latch 50, an adder 52, and an absolute magnitude circuit 56. These elements are not shown in the accompanying drawings, but are discussed in detail in the incorporated reference. The present invention is concerned with a comparison circuit which results in improved operation over the comparison circuit of the prior art devices. Basically, the comparison circuit 100 functions to generate a comparison signal on the line 102 representing the difference between two successive video signals on the line 16.

The event detector 48 includes a threshold random access memory (RAM) 58 for storing a plurality of threshold signals. Each threshold signal stored in the RAM 58 corresponds to a specific comparison signal generated by the comparison circuit 100. A diode counter 60 is utilized to select the individual threshold signal from the RAM 58 which corresponds to the present comparison signal generated by the circuit 100. The diode counter 60 can be reset to zero by a CLEAR signal and can be incremented by an INCREMENT signal. Both the CLEAR signal and the INCREMENT signal can be generated by a control logic unit 54 (not shown) of the interface 18.

The signal from the threshold RAM 58 is supplied to a complementary input of an adder 64 where it is combined with the comparison signal on the line 102. When the magnitude of the comparison signal on the line 102 exceeds the magnitude of the corresponding threshold signal, the adder 64 generates an EVENT signal to inform the interface 18 that the detector 48 has detected a defect. The adder 64 can also generate a MAGNITUDE signal to inform the interface 18 as to the difference in magnitude between the comparison signal on line 102 and the corresponding threshold signal.

Figure 2:
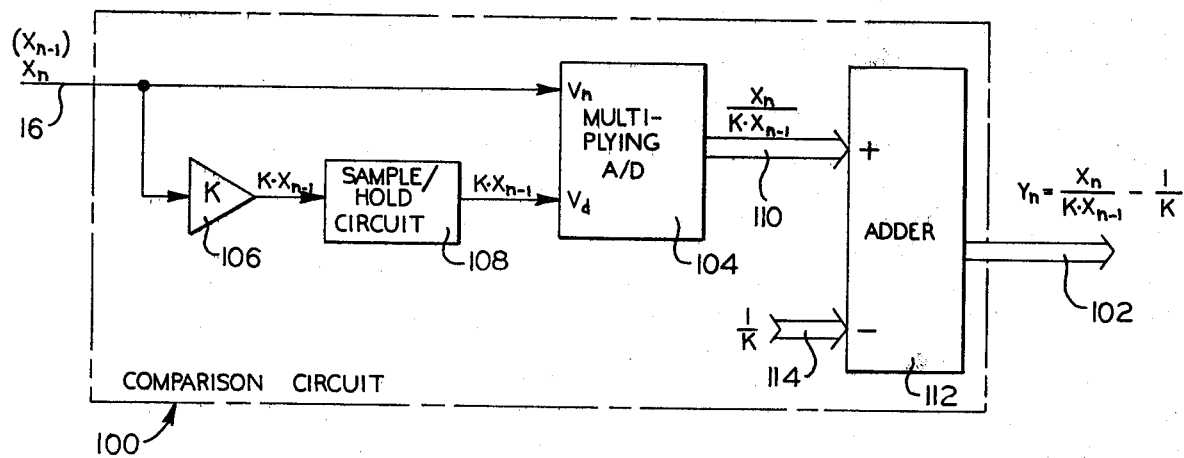
FIG. 2 is a block diagram of the comparison circuit of FIG. 1 according to the present invention.

There is shown in FIG. 2 a block diagram of the comparison circuit 100 according to the present invention. Basically, the comparison circuit according to the present invention functions to generate the comparison signal on the line 102 as the difference between two successive video signals generated on the line 16. The method according to the present invention results in a comparison signal which is insensitive to light variations across the bottle.

In FIG. 2, the video signal $X_n$ of the line 16 is supplied as an input Vn to a multiplying analog-to-digital (A/D) converter 104. The signal $X_n$ represents the light received from the present sampled pixel. The signal $X_n$ on the line 16 is also an input to an amplifier 106 which functions to multiply the signal by a first predetermined value K and generate the $K \cdot X_n$ signal as an input to a sample/hold circuit 108. The sample/hold circuit 108 functions to store the $K \cdot X_n$ signal until the next successive video signal is generated on the line 16. At this time, the value stored in the circuit 108 will be $K \cdot X_{n-1}$, where $X_{n-1}$ represents the light received from the preceeding pixel. This signal is supplied to a second input Vd of the multiplying A/D converter 104. The A/D converter 104 will then divide the $X_n$ signal by the $K \cdot X_{n-1}$ signal and convert this signal to digital form on lines 110. The lines 110 are connected to one input of an adder 112 having a complementary input connected to receive a second predetermined value 1/K on the lines 114. In the preferred embodiment of the invention, the second predetermined value 1/K is the reciprocal of the first predetermined value K, which represents the gain of the amplifier 106. The adder 112 combines the signals on the lines 110 and 114 to generate the comparison signal $Y_n$ on the line 102. Thus, the comparison signal will have a magnitude $Y_n$ which equals $(X_n/K \cdot X_{n-1}) - (1/K)$. Typically, the predetermined value K is selected to be greater than one. The above equation will be examined below to show that the comparison signal $Y_n$ is invarient to the light level common to both $X_n$ and $X_{n-1}$ and is therefore insensitive to gradual illumination variations.

In comparing the prior art method of pixel differencing to the method according to the present invention, the advantages of the present invention can be readily seen. In the prior art method of pixel differencing, the comparison signal $Y_n$ was calculated as follows: $Y_n = X_n - X_{n-1}$. Thus, if $X_n$ had a magnitude of four and $X_{n-1}$ had a magnitude of three, the comparison signal $Y_n$ would equal one for a given amount of illumination. However, if the illumination were increased by twofold, the prior art method of comparison would result in a comparison signal having a value of two. Thus, in the prior art method of pixel differencing, the light uniformity across the bottle had to remain relatively level such that similar responses were obtained for similar defects. The present invention permits a gradual illumination variation across the bottle without affecting the value of the comparison signal. For example, in the method of the present invention, if the constant K has a value of two while the signals $X_n$ and $X_{n-1}$ are equal to four and three respectively, the comparison signal $Y_n$ would equal 1/6. If the illumination were increased such that for the same defect, $X_n$ had a value eight and $X_{n-1}$ had a value of six, the comparison signal $Y_n$ would still equal 1/6. Thus, the present method results in the same comparison signal magnitude for the same defect, regardless of the light level common to both $X_n$ and $X_{n-1}$.

It should be noted that the present invention in its broadest sense encompasses the idea of dividing one video pixel signal by a second video pixel signal to generate a comparison signal which represents the ratio of the two signals. However, from a practical standpoint, it is generally not desirable to have a ratio which can cover a wide range of values. This is especially true in digital circuits where the range is limited by the number of binary lines. For example, such a ratio may result in relatively high values if the denominator is significantly smaller than the numerator. Accordingly, the present invention has incorporated the predetermined values K and 1/K into the calculation with K being a constant greater than one selected such that the value of the comparison signal will always fall between zero and a predetermined maximum. This makes the present invention readily adaptable to computer-controlled digital circuits.

Figure 3:
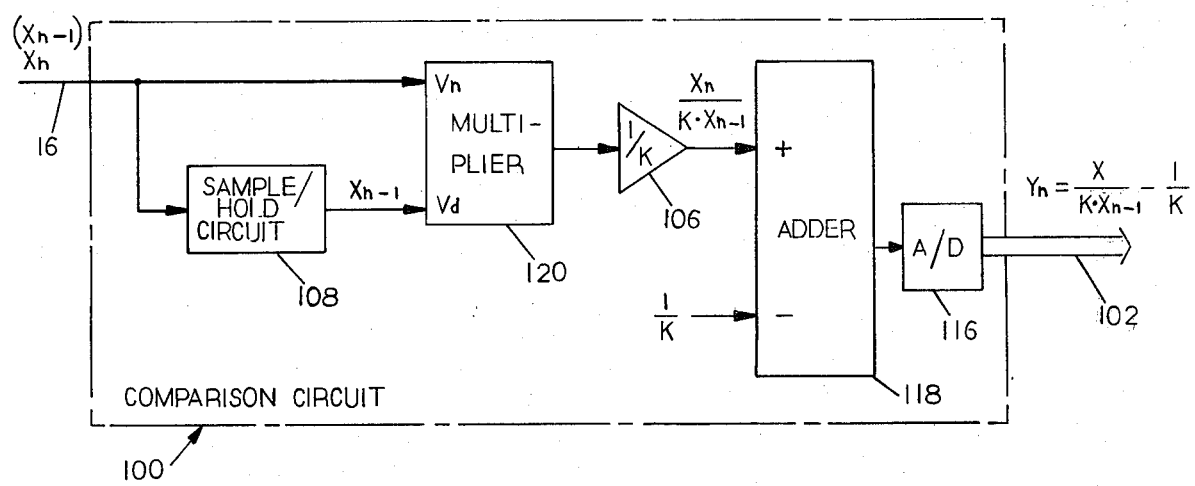
FIG. 3 is a block diagram of another comparison circuit of FIG. 1 according to the present invention.

It should also be noted that the circuit of FIG. 2 does not represent the sole method of carrying out the present invention. For example, the amplifier 106 could be connected between the line 16 and the Vd input of the A/D converter 104, while the sample/hold circuit 108 could be connected between the line 16 and the Vn input. This would result in a comparison signal having a value $Y_n = (X_{n-1}/K \cdot X_n) - (1/K)$. Also, it is not necessary that the signal be converted to digital form after the calculation of the ratio. For example, referring to FIG. 3, an A/D converter 116 is connected to the output of an analog adder 118 rather than a digital adder. In such case, the amplifier 106 having a gain adjusted to a value of 1/K is connected between a multiplier 120 and the adder 118 so that the ratio is calculated prior to the amplification by a first predetermined value of 1/K.

In accordance with the provisions of the patent statutes, the principle and mode of the operation of the invention has been explained and illustrated in its preferred embodiment. However, it must be understood that the invention may be practiced otherwise than as specifically illustrated and described without departing from its spirit or scope.

What is claimed:

1. In an apparatus for detecting defects in objects including a camera for generating a series of video signals each having a magnitude proportional to the amount of light received from a corresponding point of inspection on the object, a circuit for generating a comparison signal representing the magnitude difference between two of the video signals, said circuit comprising:
   means for multiplying one of said two video signals by a first predetermined value to generate a first product signal;
   means responsive to said first product signal and the other one of said two video signals for generating a second product signal having a magnitude representing a ratio having a denominator representing said first product signal and a numerator representing the other one of said two video signals; and
   means for subtracting a second predetermined value from said second product signal to generate the comparison signal, said second predetermined value being the reciprocal of said first predetermined value.

2. The circuit according to claim 1 including means for storing the first one of said two video signals.

3. The circuit according to claim 2 wherein said means for storing is a sample/hold circuit.

4. The circuit according to claim 2 wherein the one of said two video signals is the first of said two video signals.

5. The circuit according to claim 1 when said means for multiplying is an amplifier having a gain defined by said first predetermined value.

6. The circuit according to claim 1 wherein said means for generating said second product signal is a multiplying analog-to-digital converter such that said product signal is generated in digital form.

7. The circuit according to claim 6 wherein said means for subtracting is a binary adder having a complementary input for receiving said second predetermined value and generating said comparison signal in digital form.

8. The circuit according to claim 1 wherein said first predetermined value is greater than one.

9. A method of generating a comparison signal representing the magnitude difference between two video signals generated by an apparatus for detecting defects in objects including a camera for generating a series of video signals each having a magnitude proportional to the amount of light received from a corresponding point of inspection on the object, said method comprising the steps of:
   (a) multiplying one of said two video signals by a first predetermined value to generate a first product signal;
   (b) generating a second product signal representing the ratio between the other one of said two successive video signals and said first product signal, said second product signal having a denominator representing said first product signal and a numerator representing the other one of said two successive video signals; and
   (c) subtracting a second predetermined value from said second product signal to generate said comparison signal, said second predetermined value being the reciprocal of said first predetermined value.

10. The method according to claim 9 including the step of storing the first one of the two video signals.

11. The method according to claim 9 wherein said first predetermined value is greater than one.

12. In an apparatus for detecting defects in objects including a camera for generating a series of video signals each having a magnitude proportional to the amount of light received from a corresponding point of inspection on the object, a circuit for generating a comparison signal representing the magnitude difference between two of the video signals in said series, said circuit comprising:

means responsive to the two video signals for generating a first product signal having a magnitude representing the ratio between the two video signals;

means for multiplying said first product signal by a first predetermined value of less than one to generate a second product signal; and means for subtracting a second predetermined value from said second product signal to generate the comparison signal, said second predetermined value being equal to said first predetermined value.

13. The circuit according to claim 12 wherein said first and second predetermined values are less than one.

14. A method of generating a comparison signal representing the magnitude difference between two video signals generated by an apparatus for detecting defects in objects including a camera for generating a series of video signals each having a magnitude proportional to the amount of light received from a corresponding point of inspection on the object, the method of comprising the steps of:

(a) generating a first product signal representing the ratio between the two video signals;

(b) multiplying said first product signal by a first predetermined value of less than one to generate a second product signal; and (c) subtracting a second predetermined value from said second product signal to generate the comparison signal, said second predetermined value being equal to said first predetermined value.

15. The method according to claim 14 including the step of storing the first one of the two video signals.

* * * * *